United States Patent
Brown et al.

(10) Patent No.: US 8,574,308 B2
(45) Date of Patent: Nov. 5, 2013

(54) SYSTEMS AND METHODS FOR INSTALLING AND REMOVING AN EXPANDABLE POLYMER

(75) Inventors: Malcolm W R Brown, Leeds (GB); Horacio Montes de Oca Balderas, York (GB); Graeme I Howling, Leeds (GB); James K. Rains, Corodova, TN (US); John Rose, Collierville, TN (US); Michael Andrew Hall, Linthorpe (GB); Robin A. Chivers, York (GB); Andy Marsh, Selby (GB); Mason James Bettenga, Memphis, TN (US); Andrew Thompson, York (GB); Henry B. Faber, Memphis, TN (US)

(73) Assignee: Smith & Nephew, Inc., Memphis, TN (US)

(*) Notice: Subject to any disclaimer, the term of this patent is extended or adjusted under 35 U.S.C. 154(b) by 541 days.

(21) Appl. No.: 12/530,827

(22) PCT Filed: Mar. 13, 2008

(86) PCT No.: PCT/US2008/056836
§ 371 (c)(1),
(2), (4) Date: Feb. 26, 2010

(87) PCT Pub. No.: WO2008/112880
PCT Pub. Date: Sep. 18, 2008

(65) Prior Publication Data
US 2010/0152735 A1   Jun. 17, 2010

Related U.S. Application Data

(60) Provisional application No. 60/894,505, filed on Mar. 13, 2007, provisional application No. 60/912,684, filed on Apr. 18, 2007, provisional application No. 60/912,845, filed on Apr. 19, 2007, provisional application No. 60/989,113, filed on Nov. 19, 2007.

(51) Int. Cl.
*A61F 2/28* (2006.01)

(52) U.S. Cl.
USPC .................. 623/23.58; 606/63; 606/86 R

(58) Field of Classification Search
USPC .................................... 623/23.58–23.59
See application file for complete search history.

(56) References Cited

U.S. PATENT DOCUMENTS

| | | | | |
|---|---|---|---|---|
| 4,503,569 | A | * | 3/1985 | Dotter .................. 623/1.19 |
| 4,855,552 | A | * | 8/1989 | Marceau et al. ............. 219/630 |
| 6,127,597 | A | * | 10/2000 | Beyar et al. ................ 606/86 R |
| 6,332,885 | B1 | * | 12/2001 | Martella ...................... 606/78 |
| 2005/0080489 | A1 | * | 4/2005 | Estes et al. ................. 623/17.16 |
| 2005/0131503 | A1 | * | 6/2005 | Solem .......................... 607/96 |

* cited by examiner

*Primary Examiner* — Andrew Yang
*Assistant Examiner* — Olivia C Chang
(74) *Attorney, Agent, or Firm* — Krieg DeVault LLP

(57) ABSTRACT

The present disclosure relates to systems and methods for installing shape memory polymers relative to orthopedic implants.

20 Claims, 20 Drawing Sheets

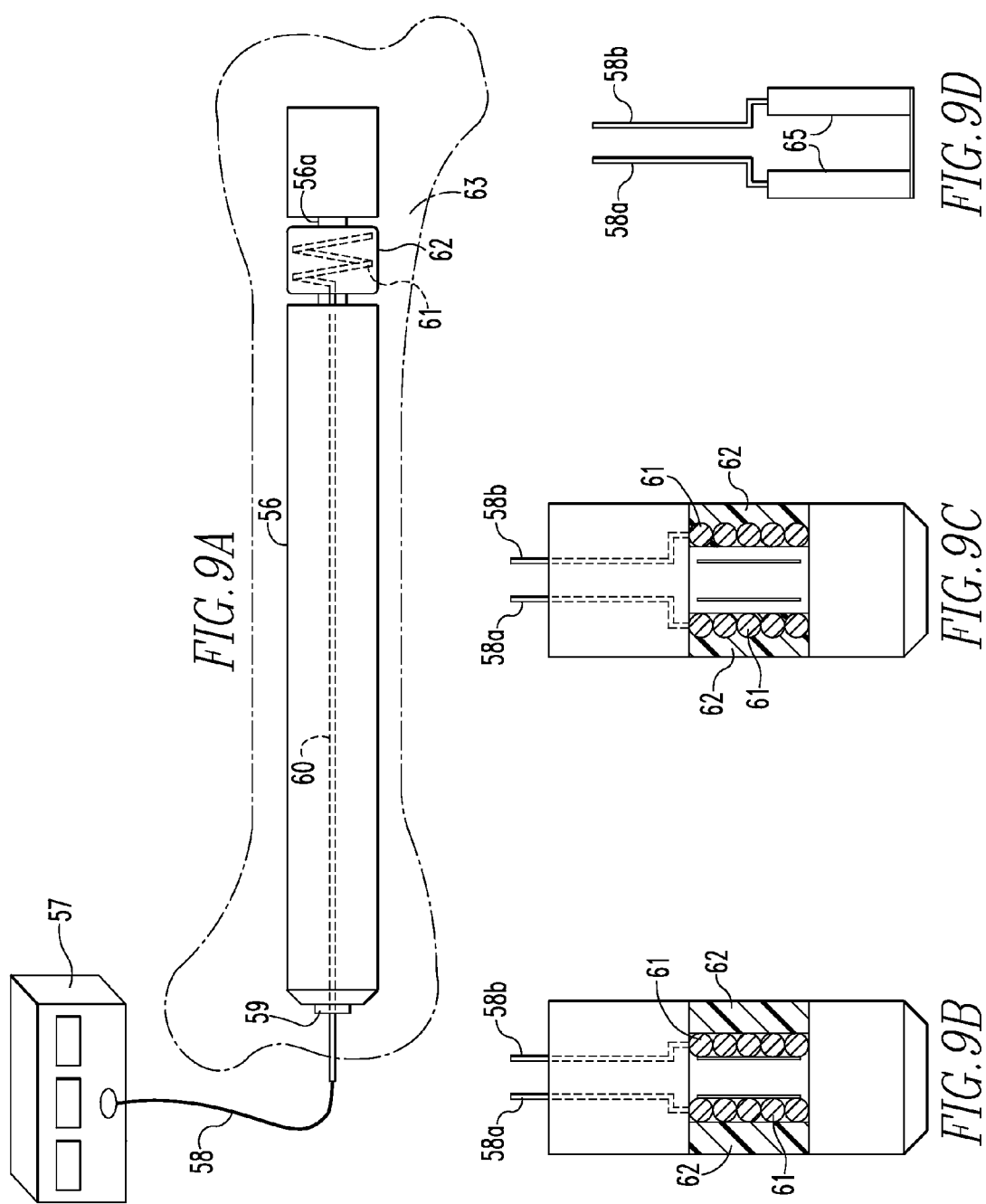

US 8,574,308 B2

SYSTEMS AND METHODS FOR INSTALLING AND REMOVING AN EXPANDABLE POLYMER

CROSS-REFERENCE TO RELATED APPLICATIONS

This application is a U.S. National Phase filing of International Application No. PCT/US2007/062757 which claims priority to U.S. Patent Application No. 60/912,845 filed on Apr. 19, 2007, U.S. Patent Application No. 60/894,505 filed on Mar. 13, 2007, and U.S. Patent Application No. 60/989,113 filed on Nov. 19, 2007, the disclosures of which are incorporated herein by reference in their entirety.

BACKGROUND OF THE INVENTION

1. Field of the Invention

This present disclosure relates generally to shape memory polymers and, more particularly, to systems and methods for installing and removing shape memory polymers.

2. Related Art

The present disclosure relates to systems and methods for installing shape memory polymers relative to orthopedic implants. The systems and/or methods may utilize chemical compounds, electromagnetic fields, fluids, thermal energy, and mechanical forces to expand the shape memory polymer for installation.

SUMMARY OF THE INVENTION

In one aspect, the present disclosure relates to an internal fixation device comprising a first component including a polymer material having shape memory qualities; and a second component coupled to the first component.

In another aspect, the present disclosure relates to a method of deforming a shape memory polymer material comprising providing a heating device including multiple heating probes; providing a shape memory polymer material including multiple holes; inserting the multiple heating probes into the multiple holes; delivering heat to the multiple heating probes, wherein the heat from the multiple heating probes causes the shape memory polymer material to deform.

In yet another aspect, the present disclosure relates to a method of deforming a shape memory polymer material comprising providing a shape memory polymer material including a through hole; inserting a tubular coil into the through hole of the shape memory polymer material; and passing a heated fluid through the tubular coil, wherein heat from the heated fluid causes the shape memory polymer material to deform.

In a further aspect, the present disclosure relates to a method comprising providing an internal fixation device having a shape memory polymer material coupled to the internal fixation device; inserting the internal fixation device into a bone; providing the shape memory polymer material with energy to expand the shape memory polymer material and fixate the internal fixation device to the bone; inserting a drill into the internal fixation device and operating the drill to remove the shape memory polymer material from the internal fixation device; and removing the internal fixation device from the bone.

In yet a further aspect, the present disclosure relates to an internal fixation device comprising a channel; a cannulated rod disposed within the channel; and a plurality of openings located at an end of the internal fixation device, wherein each opening includes a shape memory polymer material located within the opening.

Further features, aspects, and advantages of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present disclosure and together with the description, serve to explain the principles of the disclosure. In the drawings:

FIG. 9a shows a second method of fixating an internal fixation device to a bone.

FIGS. 9b-9e show cross sectional views of embodiments of the second method.

FIGS. 10b-10d show cross-sectional views of embodiments of the method of FIG. 10a.

DETAILED DESCRIPTION OF THE EMBODIMENTS

Figure 1A:
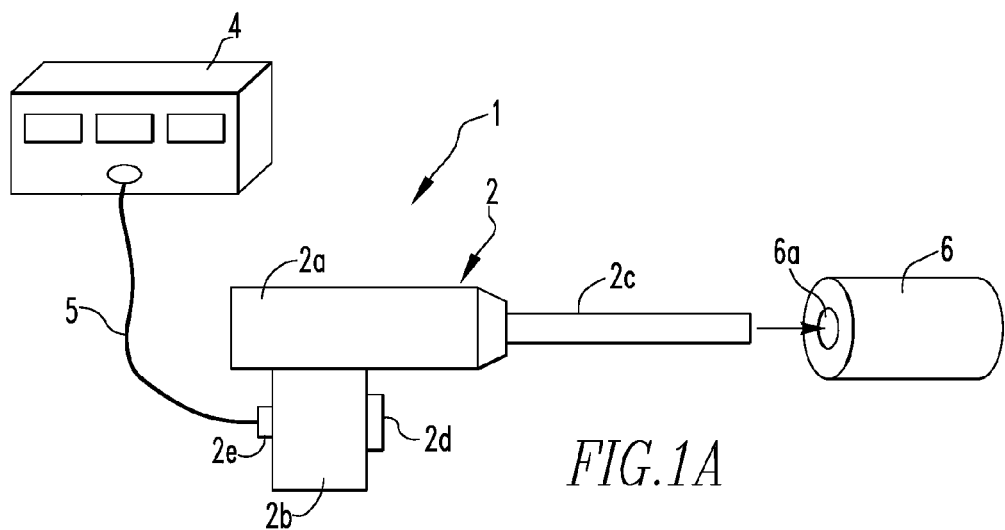
FIGS. 1a-1c show a method of delivering thermal energy to a shape memory polymer via use of a probe.

Referring to the accompanying drawings in which like reference numbers indicate like elements, FIG. 1a illustrates a method 1 of activating a sleeve of shape memory polymer material 6. The method 1 includes the use of a heating device 2 to activate the sleeve 6. The heating device 2 includes a body 2a, a handle 2b coupled to the body 2a, and a heating probe 2c coupled to the body 2a. The handle 2b may include user defined controls 2d and a connector port 2e for coupling of the device 2 to a temperature control unit 4, such as a digitally controlled potentiometer, electronic thermistor, electronic thermostat, or other temperature control unit known to one of skill in the art, via an electrical connection 5. The body 2a and handle 2b may be made of a metal, thermoplastic material, or other material known to one of skill in the art that is capable of use with the heating probe 2c. The probe 2c may be made of a metal, alloy, ceramic, or any other thereto conductive material. The sleeve 6 is cylindrical in shape and includes a through hole 6a extending the length of the sleeve 6.

Figure 1B:
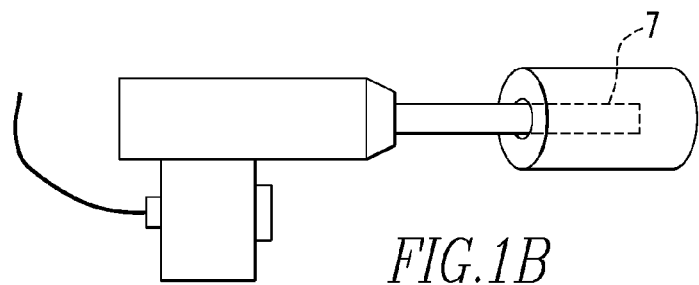
Figure 1C:
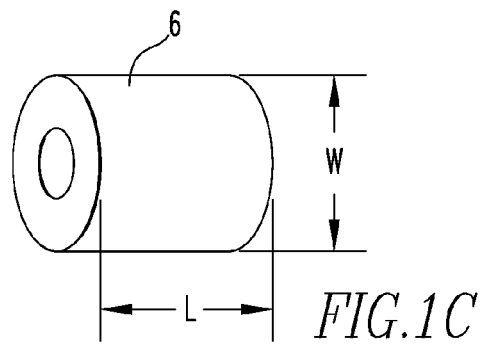

The sleeve 6 is activated by inserting the probe 2c into the through hole 6a and actuating the controls 2d to deliver heat from the temperature control unit 4 to the probe 2c and thus the sleeve 6, as shown in FIG. 1b. The control unit 4 supplies an electrical current to a cartridge heater unit located within the probe 2c, wherein the heater unit converts the current to heat via resistive heating. The probe 2c is inserted into the through hole 6a to a preferred depth 7 to ensure good thermal contact between the sleeve 6 and the heating probe 2c. The sleeve 6 retains its shape until the temperature of the probe 2c increases above the glass transition temperature of the material. Upon reaching this temperature, the sleeve 6 changes shape by decreasing in length L and increasing in width W, as is shown in FIG. 1c.

The sleeve of polymer material includes an orientated resorbable or non-resorbable material and is selected from a group that includes an amorphous polymer, a semi-crystalline polymer, or a composition having a combination thereof. Factors used to determine the type of polymer used, include, but are not limited to, the desired amount of polymer deformation, the desired rate at which that deformation occurs, the rate at which the polymer is absorbed, and the strength of the polymer.

The polymer material is processed to have shape memory qualities and therefore changes shape or deforms by shrinking axially, or along the length of the material, and expanding radially, or along the width of the material. Although, in certain instances, it is possible for the material to shrink radially and expand axially.

Generally, polymers that display shape memory qualities show a large change in modulus of elasticity at the glass transition temperature ($T_g$). The shape-memory function can be achieved by taking advantage of this characteristic. Namely, a molded article (primary molded article) to which a definite shape (the original shape) has been imparted by a common method for molding plastics, is softened by providing the article with energy and heating to a temperature ($T_f$) higher than the $T_g$ of the polymer, but lower than the melting temperature ($T_m$) thereof so as to deform it into a different shape. Next, the molded article is cooled to a temperature lower than the $T_g$, while maintaining the thus deformed shape (secondary molded article). When it is heated again to a temperature higher than the secondary molding temperature $T_f$, but lower than the $T_m$, the shape of the secondary molded article disappears and thus the article is recovered to the original shape of the primary molded article.

For the purposes of this disclosure, a molded article (i.e. the above-mentioned sleeve), having a definite shape (original shape) is formed from polymer material and is provided with energy to heat the article to a temperature above the glass transition temperature of the polymer, but lower than the melting temperature ($T_m$) thereof so as to deform it into a different shape. The glass transition temperature of the polymer material will vary based on a variety of factors, such as molecular weight, composition, structure of the polymer, and other factors known to one of ordinary skill in the art. In addition, the change in shape of the material during deformation can be tailored depending on the mode of deformation, whether this is uniaxial, biaxial, triaxial, or under tension, compression, or shear.

Specific polymers that may be used include polyetheretherketone (PEEK), polymethyl methacrylate (PMMA), polyethyl methacrylate (PEMA), polyacrylate, poly-alpha-hydroxy acids, polycapropactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof.

For the purposes of this disclosure, the polymer material is in the form of a sleeve 6 having a cylindrical structure with an outside surface that is circular and a channel 6a having a circular shape. However, the structure of the sleeve 6 and the channel 6a may have another shape, such as square, rectangular, triangular, or other shape. The sleeve 6 may be formed by die-drawing or molding (i.e. compression flow molding or thermoforming process) the above-mentioned polymers or polymer compositions. The channel 6a may be formed in the sleeve 6 during the die drawing or molding process. Alternatively, the channel 6a may be formed in the sleeve 6 post processing by drilling or by any other method of forming the channel 6a. It is also within the scope of this disclosure that the channel 6a may extend along the width or diameter of the sleeve 6 rather than the length.

Figure 2A:
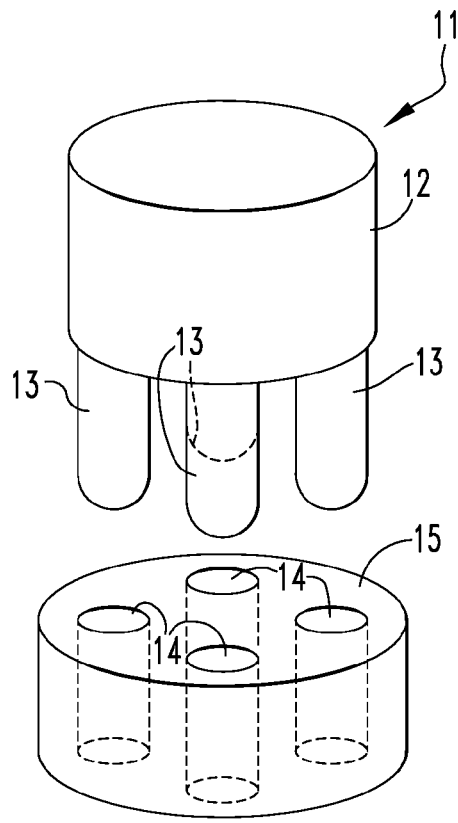
FIGS. 2a-2c show a method of delivering thermal energy to a shape memory polymer via use of a multi-pronged probe.
Figure 2B:
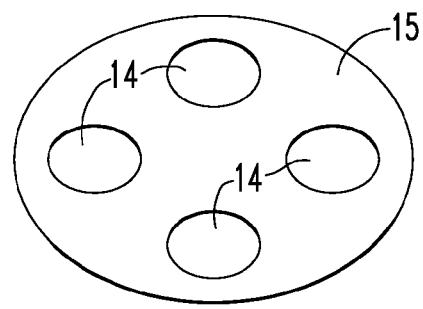
Figure 2C:
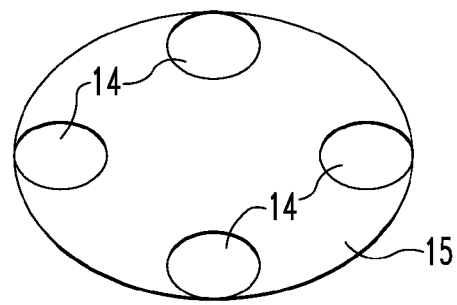

FIG. 2a shows a heater head 11 composed of a cartridge heater 12 with multiple probe attachments 13 composed of a highly conducting material such as metal, ceramics or alloys. The multiple probes are designed to fit into a component 15 having corresponding holes 14 with a diameter that is similar the diameter of the heater probes 13. The component includes a shape memory polymer material. Similar to the heating device 2 in FIG. 1, heater head 12 may be coupled to a temperature control unit via a wire for supplying heat to the probes 13. The probes 13, once deployed, interface well with the component 15 to maximize the surface area contact and ensure good heat transfer from the probes 13 to the component 15, as described above. The holes 14 may be located in central positions in the component 15, as shown in FIG. 2b, or on the periphery of the component 15, as shown in FIG. 2c. The choice of positions can be modified to tailor the relaxation profile of the polymer material 15. For instance, by heating the component material 15 from the periphery, as in FIG. 2c, improved relaxation of the polymer chains of the material 15 and hence improved mechanical properties of the polymer may be obtained due to the possibility of there being more uniform heating across the entire component 15, rather than just at the center.

The sleeves/components 6,15 described above may be used to stabilize bone fractures by inserting the sleeves/components 6,15 into the intramedullary canal of the bone, such that the sleeves/components 6,15 extend across the fracture, and providing the sleeves/components 6,15 with energy, via the method described above, to allow for radial expansion of the sleeves/components 6,15. Upon expansion, the sleeves/components 6,15 engage the inner cavity of the bone and become fixated to the bone, thereby stabilizing the fracture. Alternatively, the sleeves/components 6,15 may be used to fixate internal fixation devices, such as intramedullary nails, pins, rods, and screws, to bone, via the methods shown in FIGS. 1 and 2, as will be more fully described below.

Figure 3:
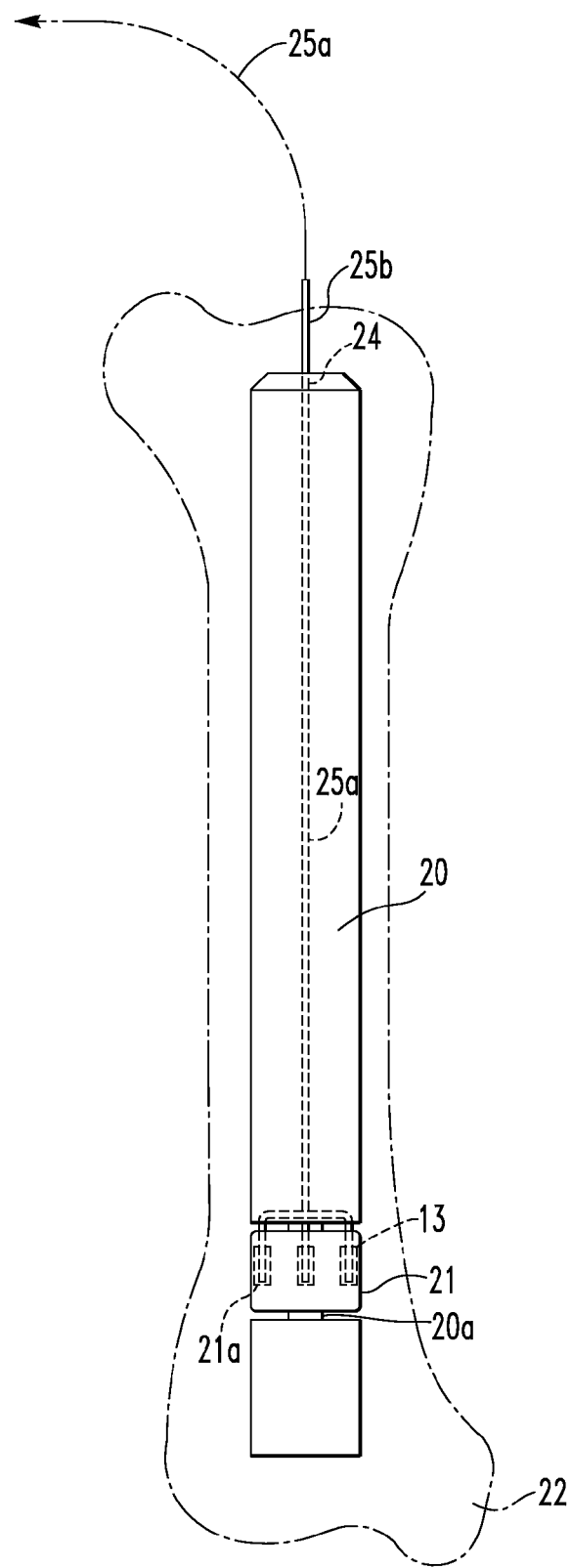
FIG. 3 shows a first method of fixating an internal fixation device to a bone.

FIG. 3 shows an embodiment of the multiple heater probe system of FIG. 2 used to lock a medical device 20, such as an intramedullary nail, into bone 22 with a shape memory polymer sleeve component 21. The component 21, similar to component 15, includes a through hole that is disposed over an area 20a of reduced diameter on the device 20. The multiple heater probes 23 are inserted into the nail 20 via an opening 24 and are connected to a control/power unit, similar to the unit 4 shown in FIG. 1a, through an extension 25a to the main body of the heater unit 25b. The heater probes 23 mate with holes 21a in the component 21, similar to the holes 14 shown in FIGS. 2a-2c, to provide good contact and heat transfer to the shape memory polymer sleeve component 21.

Alternatively, the intramedullary nail 20 may be manufactured with the heating probes 23 in-situ within the component 21. When fixation of the device 20 to the bone 22 is required, the heater probes 23 can be activated via the extension 25a, which leads to a power unit. As described above, heat transfer will occur from the probes 23 to the component 21 and the component 21 will increase in width, thereby engaging the inner cavity of the bone 22 and fixating the device 20 to the bone 22. In some applications, the component 21 may expand such that it extends through the inner cavity and into the cancellous bone.

The internal fixation device 20 may have more than one area of reduced diameter 20a, including a polymer material 21, along the length of the device 20. Also, as described above, after an article of shape memory polymer is deformed, the article is cooled and heated again to recover its original shape. However, for the purposes of this disclosure, rather than cooling the component 21 and heating it again until it recovers its original shape, the component is kept in this deformed shape so as to maintain fixation of the device to the bone. In addition, bioactive agents may be incorporated into the polymer material to be released during the deformation or the degradation of the polymer material. These agents are included to help promote bone regrowth. Examples include bone morphogenic proteins, antibiotics, anti-inflamatories, angiogenic factors, osteogenic factors, monobutyrin, omental extracts, thrombin, modified proteins, platelet rich plasma/solution, platelet poor plasma/solution, bone marrow aspirate, and any cells sourced from flora or fawna, such as living cells, preserved cells, dormant cells, and dead cells. Other bioactive agents known to one of ordinary skill in the art may also be used. Furthermore, the polymeric materials can be formed as a composite or matrix and include reinforcing material or phases such as fibers, rods, platelets, and fillers. For example, the polymeric material can include glass fibers, carbon fibers, polymeric fibers, ceramic fibers, or ceramic particulates. Other reinforcing material or phases known to one of ordinary skill in the art could also be used.

Figure 4A:
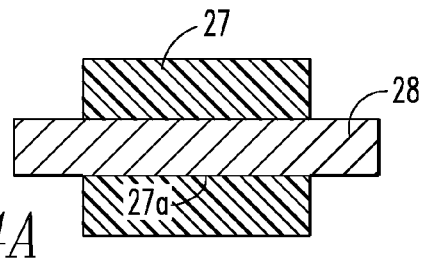
FIGS. 4a-4b show a cross-sectional view of an embodiment of the method shown in FIGS. 1a-1c.
Figure 4B:
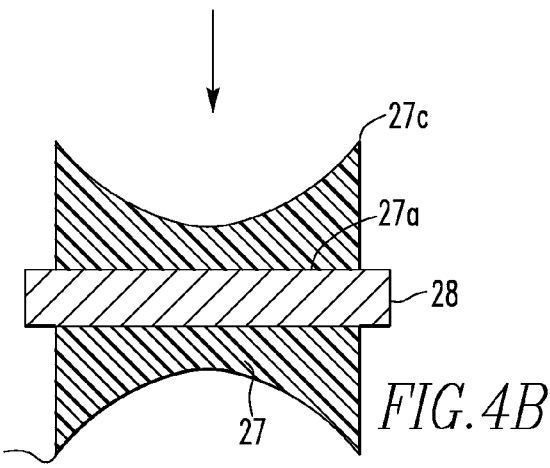

FIG. 4a depicts a cross sectional view of a sleeve 27 of shape memory polymer material, similar to the sleeves 15,21 shown above. A heat conducting probe 28 is inserted into the through hole 27a of the sleeve 27. Upon heating, the material 27 relaxes unevenly, as shown in FIG. 4b, with a greater relaxation towards either end 27b,27c of the material 27. The friction present between the probe 28 and the polymer material 27 substantially reduces the relaxation of the polymer chains and thereby the expansion of the polymer material 27.

Figure 5A:
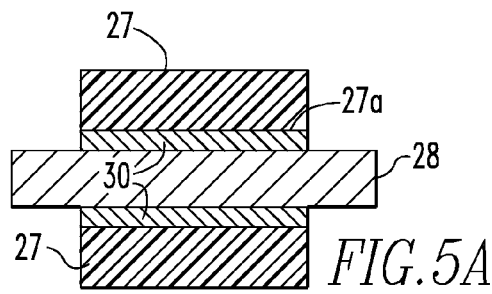
FIGS. 5a-5b show a cross-sectional view of a method of delivering thermal energy to a shape memory polymer via use of a probe having a low friction coating.
Figure 5B:
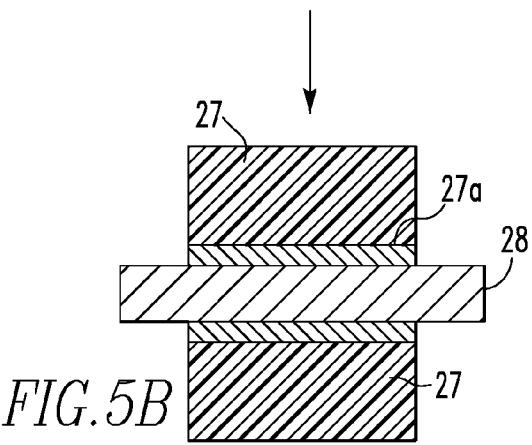

FIG. 5a depicts a cross sectional view of a modified heating probe 28 in the sleeve 27. A heat conducting probe 28 with a low friction coating 30 is inserted into the through hole 27a. Upon heating, the sleeve 27 expands more evenly due to the reduction in adhesion between the sleeve 27 and the heating probe 28, as shown in FIG. 5b FIGS. 6a-6c depict modifications of the heating probe by changing the coefficient of friction ($\mu$) of different zones of the probe 30. The coefficient of friction is defined by the equation $F=\mu P$ where the letter F equals the force required to overcome friction and P is the normal force exerted by the polymer material on the surface of the heating probe. Depending on the material used to make the heating probe and any other components that may be placed on the surface of the probe, the coefficient of friction ($\mu$) may be between about 0.0001 to about 5. By a selection of materials with different coefficients of friction, it may be possible to tailor the friction profile across the probe.

Figure 6A:
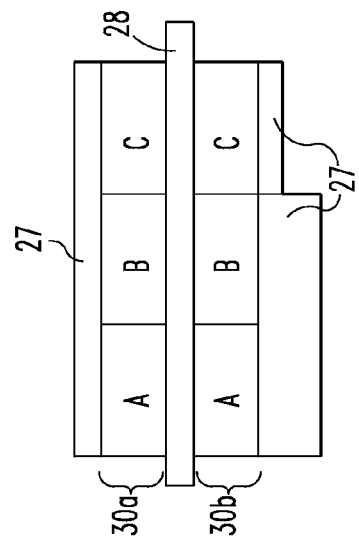
FIGS. 6a-6c show cross-sectional views of methods of delivering thermal energy to a shape memory polymer via use of a probe having multiple coatings.

FIG. 6a depicts a heat conducting probe 28, with a surface having a modified amount of friction 30, inserted into a through hole 27a following relaxation. The surface includes component A having a low amount of friction thereby allowing a greater relaxation rate of the shape memory polymer material 27, component B having a medium amount of friction thereby allowing a lesser relaxation rate of the shape memory polymer material 27 compared to component A, and component C having a high amount of friction thereby allowing a minimal relaxation rate of the shape memory polymer material 27. In this example, the coefficient of friction for A, B, and C may be expressed by the following:

$$\mu \text{ of A} < \mu \text{ of B} < \mu \text{ of C}$$

Figure 6B:
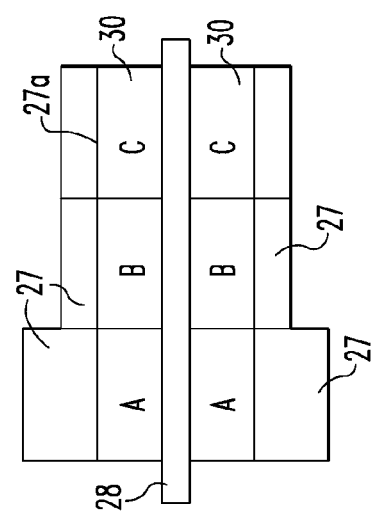

FIG. 6b depicts a heat conducting probe 28, with a surface having a modified amount of friction 30, inserted into a through hole 27a following relaxation. The surface of the probe 28 includes component A having a low amount of friction thereby allowing a greater relaxation rate of the shape memory polymer material 27 and components B and C, both having a medium amount of friction, thereby allowing a lesser relaxation rate of the shape memory polymer material 27 compared to component A.

Figure 6C:
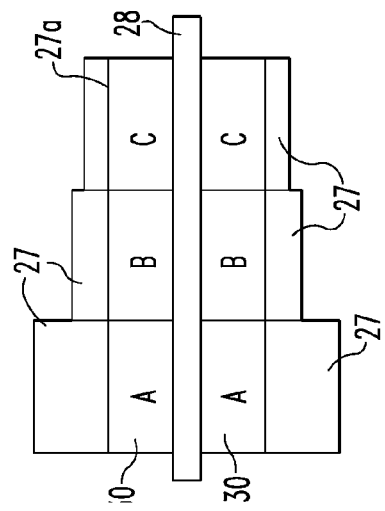

FIG. 6c shows a heat conducting probe 28, having a modified surface fiction 30, inserted into a sleeve 27 following relaxation. The surface friction coefficient is modified in two areas 30a,30b containing alternative components or surface finishes A, B, and C. In the first region 30a, component A, B, and C have a composition or finish that has a high coefficient of friction thereby allowing minimal relaxation rate of the shape memory polymer material 27. In the second region 30b, components A and B have a low coefficient of friction thereby allowing a greater relaxation rate of the shape memory polymer material 27 and component C has a high coefficient of friction composition allowing a minimal relaxation rate of the shape memory polymer material.

The low, medium, and high amounts of friction described above are relative to each other in terms of a value to be placed on the particular amount of friction. For the purposes of this disclosure, the amounts are separated by a coefficient of friction that ranges from between about 0.05 to about 0.2. For example, in FIG. 6a, component A, which has a low amount of friction, may have a value of 0.01, component B, which has a medium amount of friction, may have a value of 0.06, and component C, which has a high amount of friction, may have a value of 0.11.

A high or medium friction surface may be achieved in a number of ways. For instance, a surface texture may be machined or etched onto the probe, wherein the friction generated is dependent on the roughness of the surface texture applied. In addition, coating the probe with a material containing particles may also produce a surface having a high or medium friction. The amount of friction is dependent on the size and number of the particles in the coating. Thus, the larger the particle, the higher the amount of friction will be on the surface of the probe and the higher the concentration, the higher the amount of friction will be on the surface of the probe. The particle coatings may be applied by painting, dipping, or electrostatic powder coating. Alternatively, the areas of different friction can be produced by coating or manufacturing regions of the probe from different materials.

A low friction region of the probe can be produced by a coating, sleeve, or a section of the probe made from a polymer, such as PTFE, PFA, FEP, or a ceramic having low friction properties. The coating may be applied by electrostatic powder coating and the sleeves or sections may be produced by molding or machining. In addition, the sleeves may be applied as one sleeve having discrete zones of friction along the length of the sleeve or as several sleeves with each sleeve having a particular amount of friction. Alternatively, a low friction region can be produced by applying a lubricant such as an oil or grease to a region of the probe. Also, polishing the surface of the probe to a mirror finish may produce a low friction region.

Figure 7:
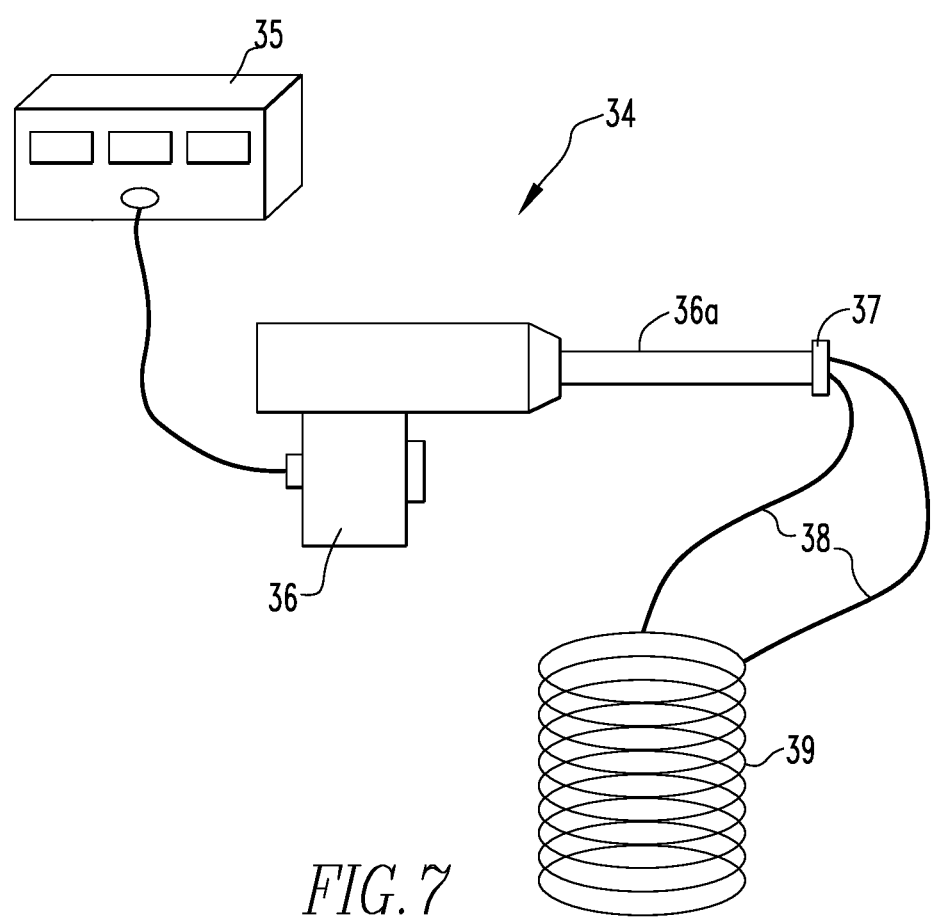
FIG. 7 shows a method of delivering thermal energy to a shape memory polymer via use of a heating coil circuit.

FIG. 7 shows a heating system 34 for a shape memory polymer material. The heating system 34 includes; a control/power unit 35 which contains the necessary temperature and timing control means, and a heating device 36, similar to the device 2 in FIG. 1, connected via a connector 37 to a heating coil circuit 39. The connector 37, which may be a pin and socket connector, conductive silicon, or other type of male/female connector, allows for an electrical current from the power unit to be conducted across wires 38 and delivered to the coil circuit 39. The coil 39 may include a high resistant conductor or other type of heating element. In addition, the conductor may or may not be insulated. Alternatively, the heating coil 39 may be contained within the heating probe 36a. In addition, the heating coil 39 may be placed directly within shape memory polymer articles/components, such as those described above, and coupled directly via connector 37 to the control/power unit 35 without the need for the device 36. Due to the larger surface area of the heating coil circuit 39 and therefore more contact between the circuit 39 and the shape memory polymer material, the heating system 34 has numerous advantages including the improved distribution of heat to the shape memory polymer material allowing for improved relaxation properties.

Figure 8A:
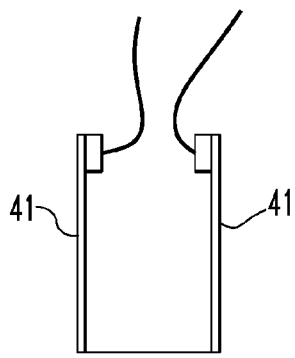
FIGS. 8a-8d show embodiments of the method of FIG. 7.
Figure 8B:
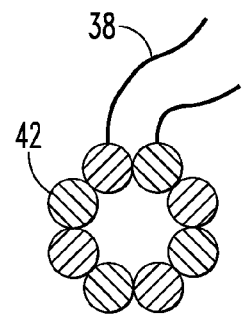
Figure 8C:
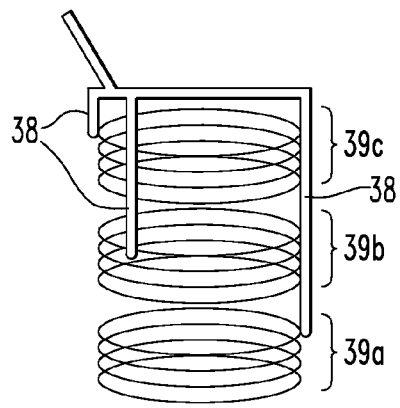
Figure 8D:
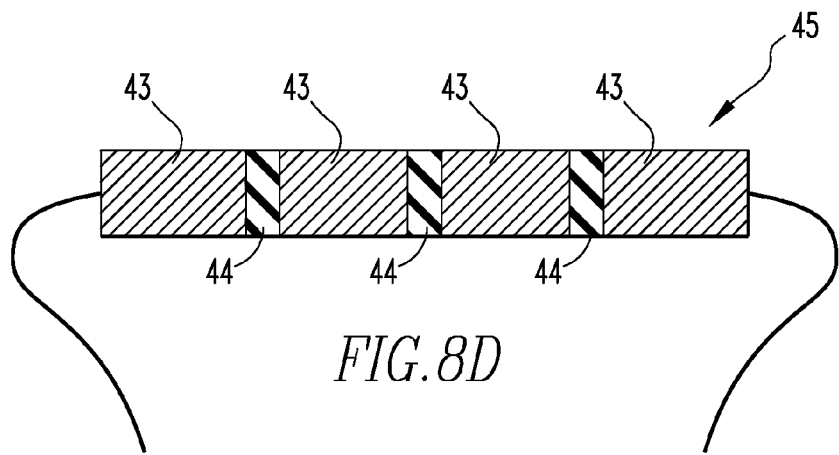

FIGS. 8a-8d show alternative embodiments for the heating coil device depicted in FIG. 7. FIG. 8a depicts a cross sectional view of conductive heating strips 41 that may be coupled to the device described in FIG. 7. FIG. 8b depicts a vertical cross sectional view of a circular arrangement of longitudinal heating rods 42 connected via 38 to the device described in FIG. 7. FIG. 8c depicts a segmented heated coil that allows for the controlled heating of desired areas of a shape memory polymer material. The heating coils are arranged into segments comprising lower 39a, central 39b, and higher regions 39c connected via wires 38 to the device described in FIG. 7. By varying the coil segment heating, the relaxation of the shape memory polymer can be managed in a controlled manner. FIG. 8d depicts a cross-section of a device 45 including alternative regions 43,44 of heated segments 43 with interconnecting insulated regions 44. The segmental heating device 45 shown in FIG. 8d provides a controlled system for relaxing the shape memory polymer material. For instance, if the device 45 in FIG. 8d was located in the through hole 6a of the sleeve 6 described above, each of the heated segments 43 may be provided with a different temperature, at the same or different times, to allow for a controlled relaxation of the polymer material. This controlled relaxation may allow the user to control fixation of the sleeve to bone and controlled compression of a bone fracture. The devices 39, 41, 42, 45 in FIGS. 8a-8d may be located within the shape memory polymer material, on or within an internal fixation device, or in the probe of the heating device 36 shown in FIG. 7.

FIG. 9a shows an internal fixation device 56, similar to the internal fixation device 20 shown in FIG. 3, with a sleeve 62 of shape memory polymer material coupled to an area of reduced diameter 56a. A power control source 57 is capable of delivering an electric current via cable 58 to a connector 59. The electric current is carried, from the connector 59, via a conductor 60, to heating coils 61 located in proximity of the sleeve 62, as further described below, such that the heating coils 61 are capable of providing heat to the sleeve 62 and relaxing the shape memory polymer material 62. Upon relaxation, the shape memory polymer material 62 expands and engages the interface between the shape memory polymer material 62 and the surrounding bone 63 thereby fixating the device 56 to the bone 63.

FIGS. 9b-9e show alternative arrangements of FIG. 9a. FIG. 9b shows heater coils 61 manufactured within the intramedullary fixation device 56 that are capable of being coupled to an external control/power source by wires 58 and relaxing the shape memory polymer sleeve 62. FIG. 9c is similar to FIG. 9b except for the heating coils 61 are manufactured/embedded within the shape memory polymer sleeve 62 and are coupled to an external control/power source by wires 58.

FIG. 9d and FIG. 9e show alternative configurations including the use of conductive strips 65, which may be arranged as discussed in FIGS. 9b and 9c and coupled to an external control/power source by wires 58.

The wires 58a,58b are configured such that wire 58a delivers electrical current to the heating elements from unit 57 and wire 58b returns electrical current from the heating elements to the unit 57. However, other configurations are possible.

Figure 10C:
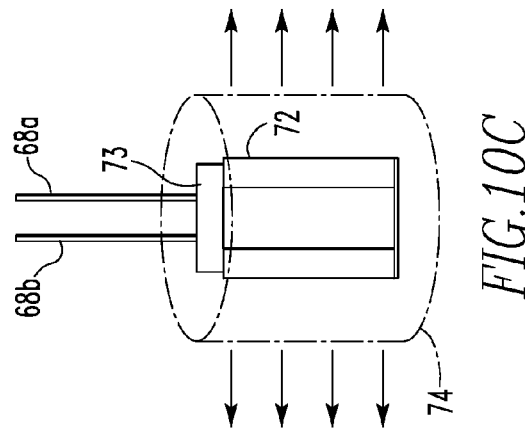
Figure 10B:
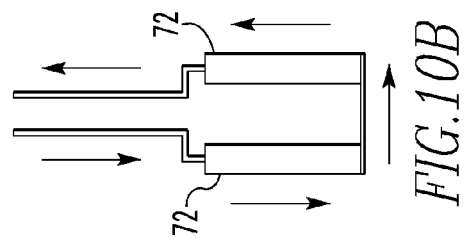
Figure 10D:
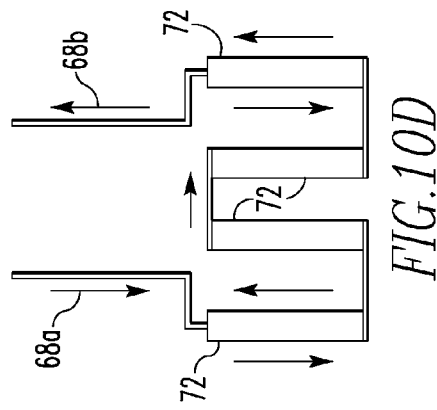
Figure 10A:
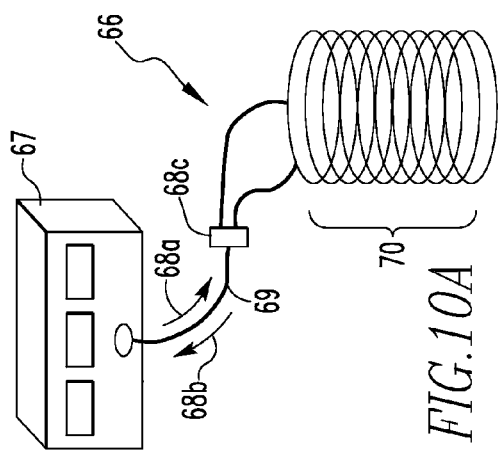
FIG. 10a shows a method of delivering thermal energy to a shape memory polymer via use of a fluid heater system.

FIG. 10a shows a fluid heater system 66 that may be used to provide heat to a shape memory polymer material. The device includes a control/power source 67 that may contain components, such as a temperature regulator, pumps, heater, and a timer. The heating fluid circuit 70 is coupled to the source 67 via tubing 68 that has a flow 68a and a return 68b mechanism. The tubing 69 is coupled to the heating circuit 70 by a connector 68c. Fluid is pumped via source 67 through the tubing 69 into the heating circuit 70, before returning via return mechanism 68b to the control source 67. The heating circuit 70 and flow 68a and return 68b mechanisms includes hollow tubes that allow for the flow of fluid through the tubes. Tubing 69 and the tubes of the circuit 70 and flow and return mechanisms 68a, 68b may be constructed of plastics, metals, alloys, and ceramics.

FIGS. 10b-10d show alternative embodiments for the fluid heating system 66 shown FIG. 10a. FIG. 10b shows vertical heating rods 72 that are capable of circulating hot fluid. FIG. 10c shows heating rods capable of circulating hot fluid 72 manufactured within a shape memory polymer component 74. The rods 72 are connected to a hot fluid supply by removable connectors 73 to a fluid flow 68a and a fluid return 68b. The fluid flow and returns 68a,68b are connected to a power/ control device, such as 67 in FIG. 10. FIG. 10d shows multiple heating rods 72 capable of circulating hot fluid with a fluid flow 68a and fluid return 68b. The embodiments shown in FIGS. 10b-10d may be located in an internal fixation device that has a shape memory polymer coupled to it, such as the device 20,56 shown in FIGS. 3 and 10a, or embedded within the polymer itself.

Figure 11C:
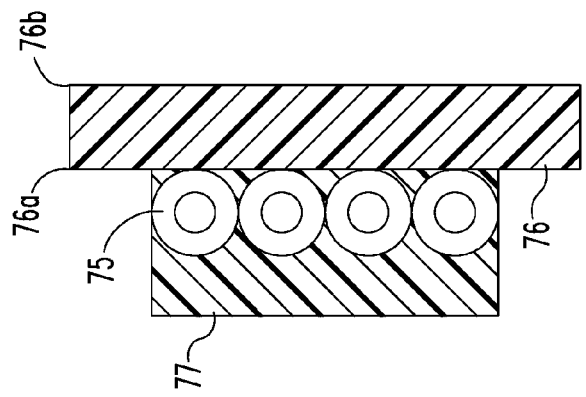
FIG. 11c shows a cross-sectional view of one half of a third internal fixation device of the present disclosure.
Figure 11B:
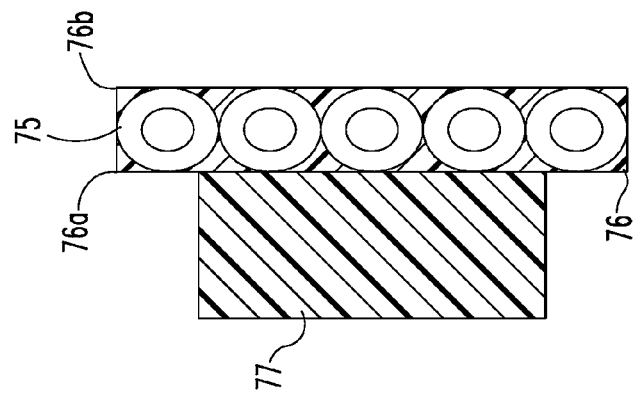
FIG. 11b shows a cross-sectional view of one half of a second internal fixation device of the present disclosure.
Figure 11A:
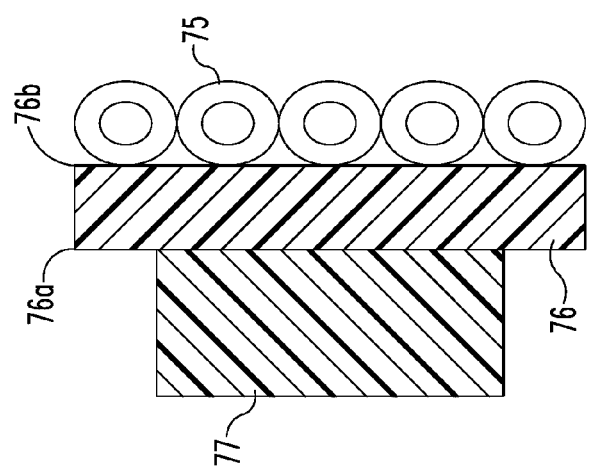
FIG. 11a shows a cross-sectional view of one half of a first internal fixation device of the present disclosure.

FIG. 11a shows one half of a medical device 76, such as an intramedullary nail, having internal 76b and external 76a surfaces with shape memory polymer material 77 coupled to the external surface 76a. Contained within the medical device 76 are tubes 75 capable of carrying hot fluid, which transfer heat/energy from the fluid through the inner 76b and outer surface 76a of the medical device 76 to the shape memory polymer material 77, hence relaxing the material 77.

FIG. 11b, which is similar to FIG. 11a, shows tubes 75, located between the inner 76b and outer 76a surface of the medical device 76, that are capable of carrying hot fluid, which transfer heat/energy from the fluid through the outer surface 76a of the medical device 76 to the shape memory polymer material 77, hence relaxing the material 77.

FIG. 11c, which is similar to FIG. 11a and FIG. 11b, shows tubes 75 within the shape memory polymer material 77 that are capable of carrying hot fluid, which transfer heat/energy from the fluid to the shape memory polymer material 77, hence relaxing the material 77.

Figure 12A:
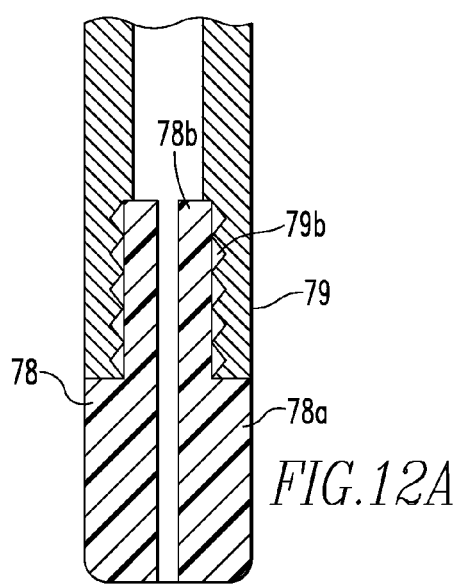
FIGS. 12a-12d show a first method of fixating and removing an internal fixation device to and from a bone.
Figure 12B:
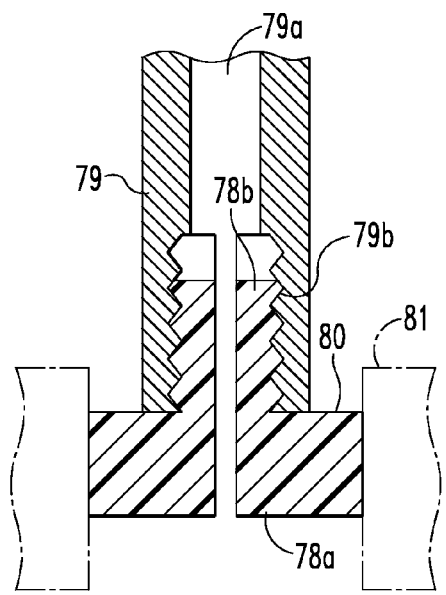

FIGS. 12a and 12b show an internal fixation device 79, such as an intramedullary nail, having a channel 79a partially extending the length of the device 79. The channel 79a, which includes a threaded inner wall 79b, may be of a variety of lengths and widths. In addition, the inner wall 79b of the channel 79a may include a feature other than threads or may be smooth. A polymer material 78, including a body 78a having a stem portion 78b, is coupled to the device 79, such that the stem portion 78b is located within the channel 79a. As shown above, once the device 79 is inserted into a bone 81, the polymer material 78 is deformed, via one of the methods described above or another method known to one of ordinary skill in the art, to expand the material 78 radially and fixate the device 79 to bone 81. The stem portion 78b of the material 78 also expands radially to engage the threaded inner wall 79b and fixate the material 78 to the device 79.

Figure 12C:
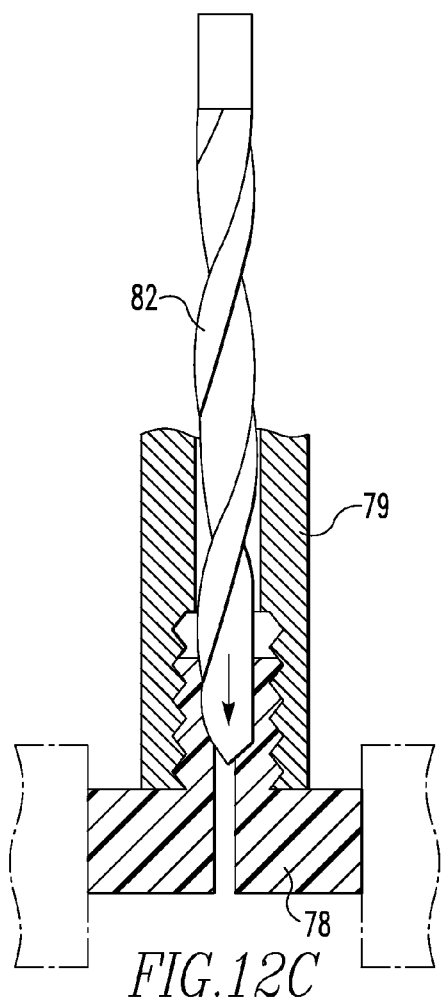
Figure 12D:
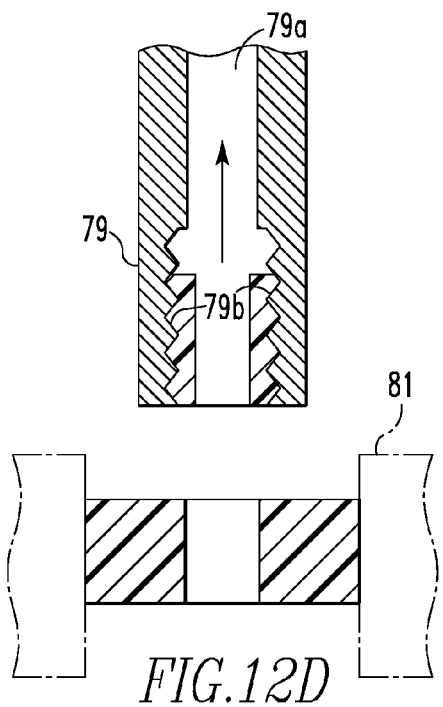

As shown in FIGS. 12c and 12d, removal of the device 79 can be facilitated by drilling out the material 78, via the use of a drill 82, to destroy the locking of the material 78 with the device 79. The device 79 can them be removed leaving residual material 78 bound to the threaded inner wall 79b. With the device 79 removed, the remaining material 80 can be reamed out of the bone 81 using a reamer or drill type tool.

Figure 13A:
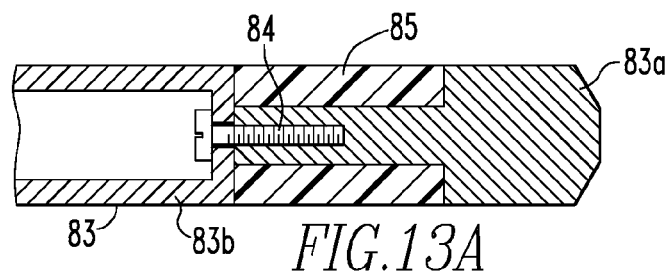
FIGS. 13a-13c show a second method of fixating and removing an internal fixation device to and from a bone.
Figure 13B:
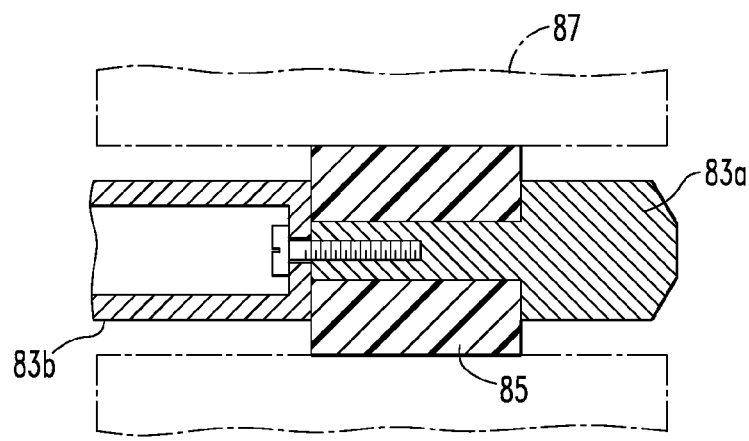
Figure 13C:
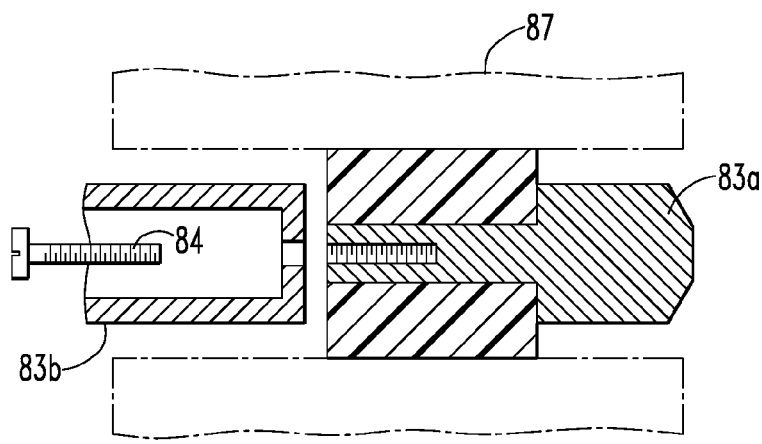

FIGS. 13a-13c show another internal fixation device 83 including a shape memory polymer sleeve 85 mounted onto a first component 83a, which is detachable from the second component 83b, by means of a mechanical joiner 84, such as a screw or other mechanical interlock.

The shape memory polymer sleeve 85 is heated, via a heating method described above or other method known to one of skill in the art, to expand the sleeve 85 and lock the device 83 into bone 87, as shown in FIG. 13b. Removal of the device 83 from the bone 87 can be facilitated by removing or unlocking the mechanical joiner 84. This enables the second component 83b to be removed and leaves the shape memory polymer material 85 and first component 83a in the bone 87, as shown in FIG. 13b. The shape memory polymer 85 is then removed by reaming or drilling and the first component 83a may then be freed. Alternatively, the first component 83a may be removed and the shape memory polymer 85 may remain in the bone 87 to be gradually reabsorbed by the body.

Figure 14A:
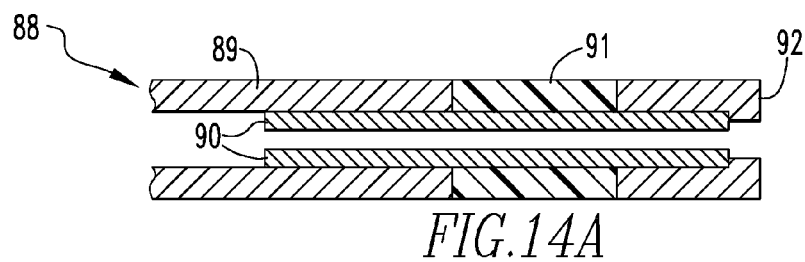
FIGS. 14a-14d show a third method of fixating and removing an internal fixation device to and from a bone.
Figure 14B:
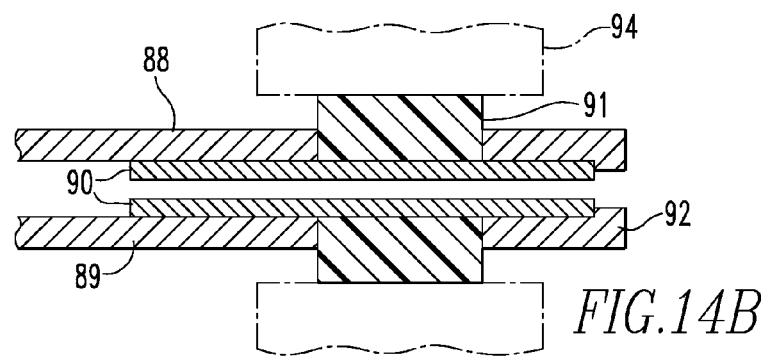

FIGS. 14a-d show a fixation device 88 including a sleeve 91 of shape memory polymer material mounted into a multi-component post 89,92 which has a removable central core component 90 around which the sleeve 91 is housed. This core component 90 is mechanically locked in place in the device 88. The central core component 90 can be cannulated to enable heating of the shape memory polymer sleeve 91 via use of a heater that would be inserted into component 90. Other heating devices can also be used such as heaters built into the core 90 or into the material 91. The heating causes the material 91 to expand and engage the bone 94, thereby fixating the material 91 to bone 94, as shown in FIGS. 14a-14b.

Figure 14C:
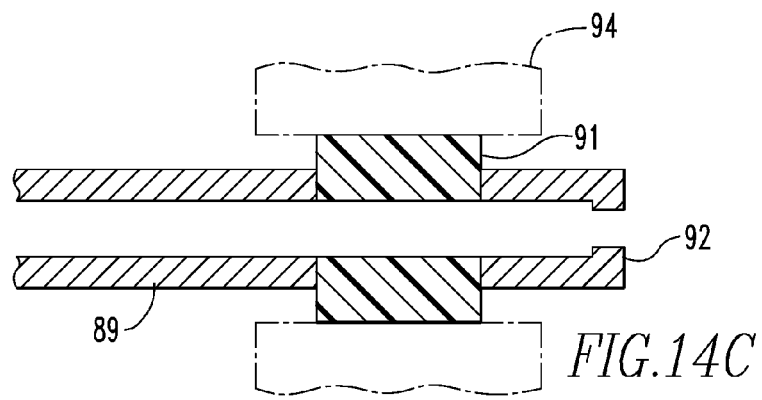
Figure 14:
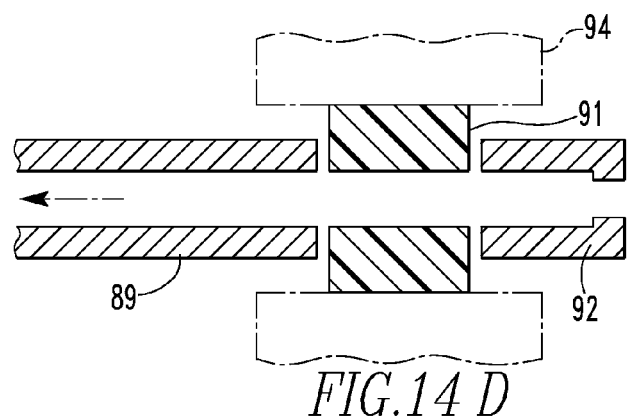

As shown in FIGS. 14c-14d, removal of the device 88 is enabled by removing the central core component 90. The central component 90 is unlocked by mechanisms, such as unscrewing or mechanical disengagement, thereby allowing the post components 89,92 to become free of the bone 94 and removed. The material 91 is then removed by reaming or drilling and any remaining component of the device 88 can be then be removed. Alternatively, the material 91 remains in the bone 94 and is eventually reabsorbed by the body.

Figure 15A:
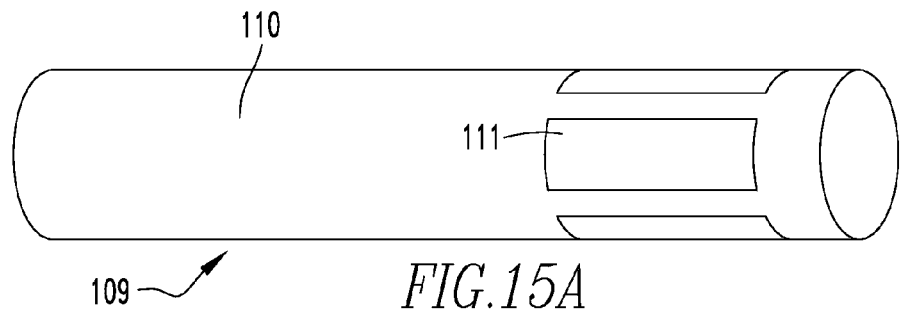
FIGS. 15a-15d show a method of activating and removing an internal fixation device.
Figure 15B:
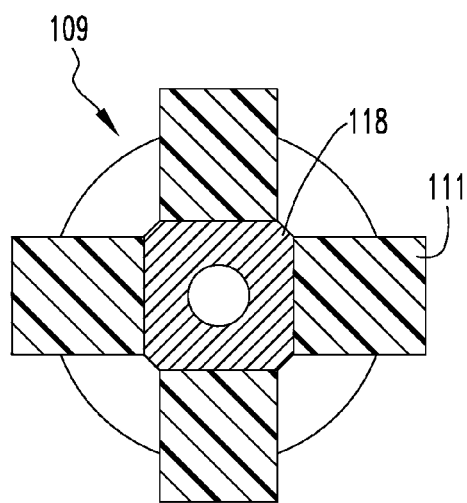
Figure 15C:
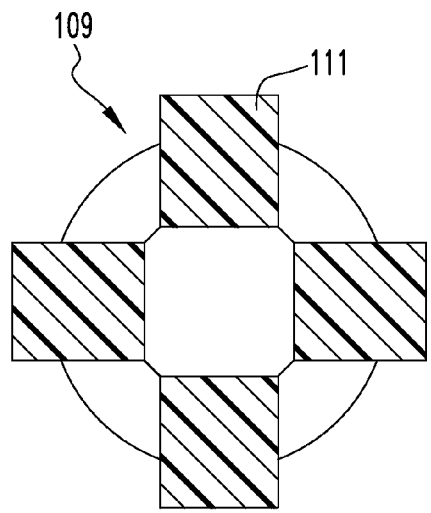
Figure 15D:
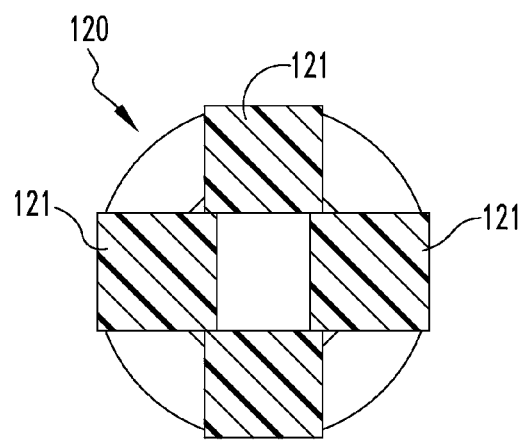

As shown in FIGS. 15a-15d, this concept can be extended to include a single component medical device 109 including a body 110 with shape memory polymer components 111. The body 110 is cannulated and includes a core component 118, similar to core component 90 in FIGS. A-14d. The core component may be cannulated to enable the application of heat to initiate expansion of the shape memory polymer components 111 as shown in FIG. 15(b). Removal of the medical device 109 may be facilitated by removal of the core component 118, enabling the shape memory polymer components 111 to translate radially inward and disengage from the bone, thereby allowing the whole device 109 to be disengaged and removed in one piece.

Figure 16A:
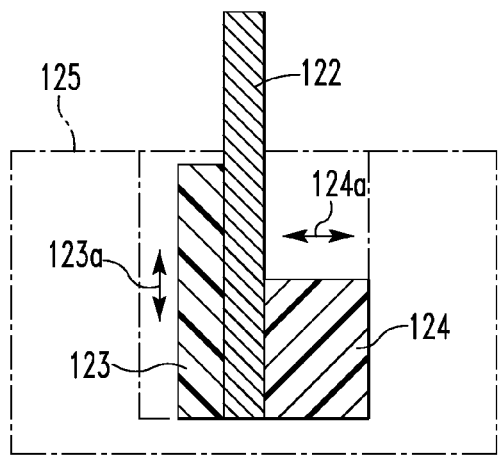
FIGS. 16a-16c show a fourth method of fixating and removing an internal fixation device to and from a bone.
Figure 16B:
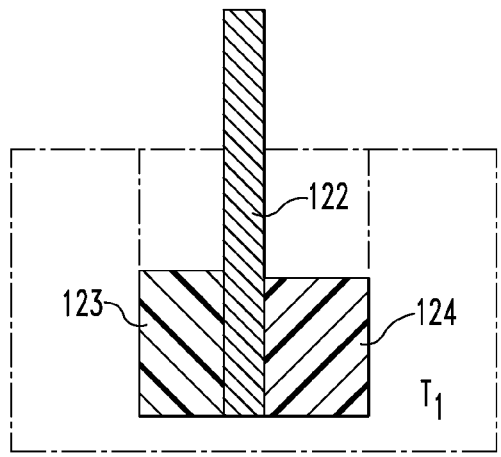
Figure 16C:
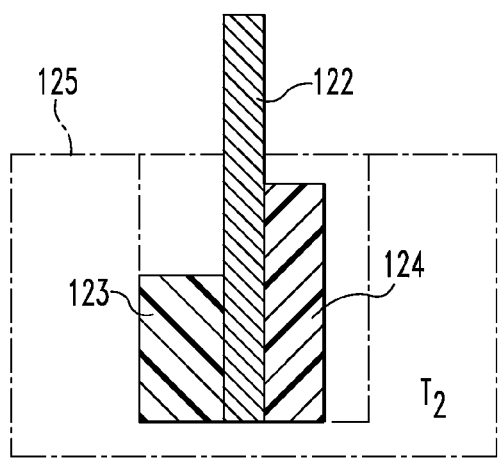

As shown in FIGS. 16a-c, two different shape memory polymer materials 123,124 may be used with a medical device 122 for fixation and removal of the device 122 from bone 125. The materials 123,124 include different activation temperatures (i.e. Tg) and directions of orientations, such that material 123 has been orientated in the directions shown by 123a and material 124 has been orientated in directions shown by 124a, as shown in FIG. 16a. When the materials 123,124 are heated to temperature T1, expansion of material 123 occurs radially and results in fixation of the device 122 to bone 125. Likewise, when the materials 123,124 are heated to temperature T2, material 124 expands axially causing the device 122 to become sufficiently loose from the bone and facilitate removal of the device 122.

As noted above, the shape memory polymer materials 123, 124 have different activation temperatures and may be uniaxial, biaxial, or triaxial drawn. The shape memory polymer materials are combined in such a fashion that the outer surface of one of the materials 123 expands in a radical direction at temperature T1 and the outer surface of second material 124 decreases in the radial at temperature T2. The materials 123,124 may be resorbable and/or non-resorbable. In addition, the materials 123,124 may contain materials which influence the physical (orientation, mechanical, relaxation, activation, and expansion), chemical (i.e. degradation), and/or biological properties (i.e. host response, tissue regeneration on or around construct/device when in used in vivo) of the materials. The materials 123,124 may be arranged such that the materials are used as separate strips that are coupled to the device 122 or are joined together by a chemical, i.e. glue, or physical, i.e. mechanical locking, means.

Figure 17A:
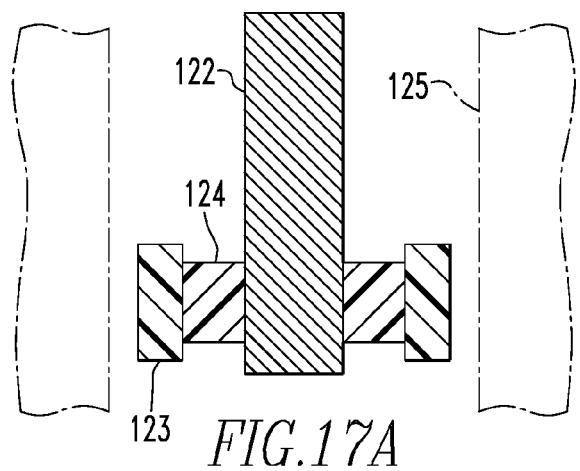
FIGS. 17a-17c show a fifth method of fixating and removing an internal fixation device to and from a bone.
Figure 17B:
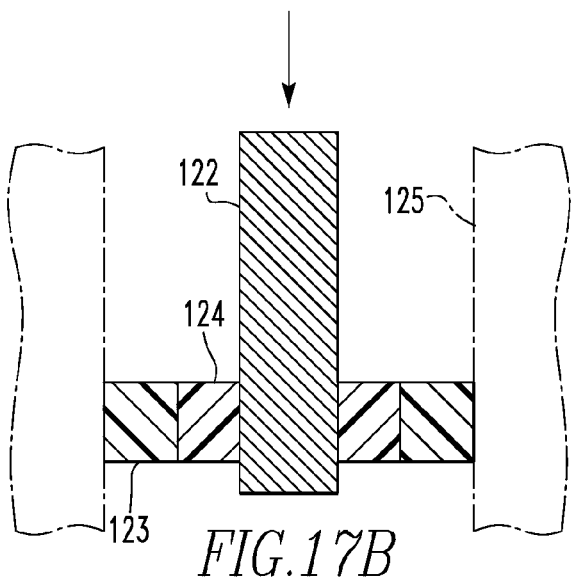
Figure 17C:
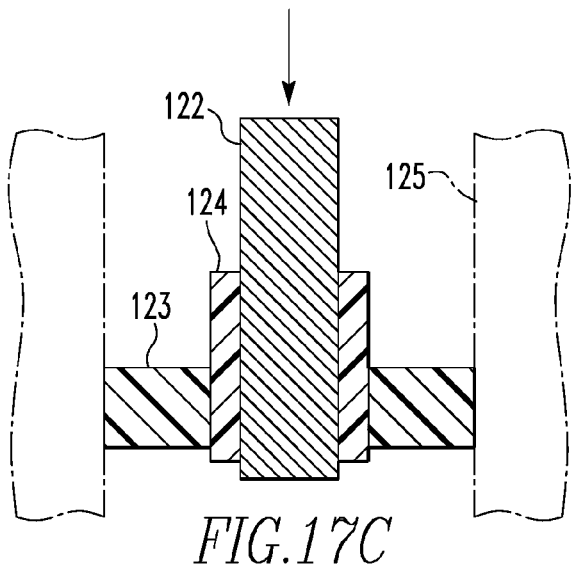

As shown in FIGS. 17a-c, materials 123,124 have been orientated in such a manner that the orientation of the polymer chains in material 123 is at an angle of 90° from the orientation of the polymer chains in material 124. Optimum results may be obtained when the materials 123,124 are orientated in this manner, as shown in FIGS. 18a-18c.

Figure 18A:
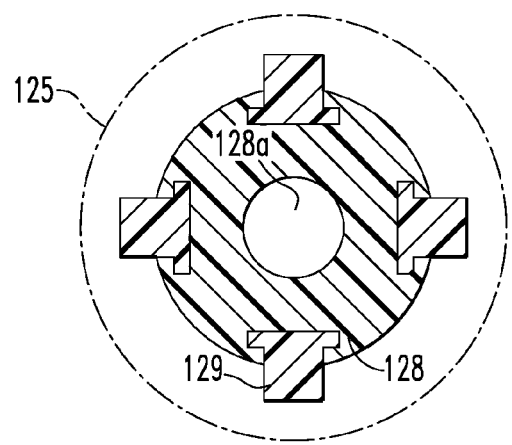
FIGS. 18a-18c show a sixth method of fixating and removing an internal fixation device to and from a bone.
Figure 18B:
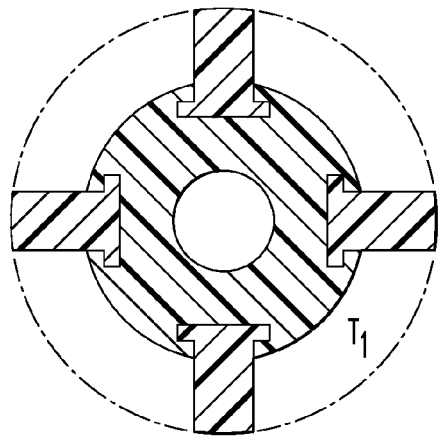
Figure 18C:
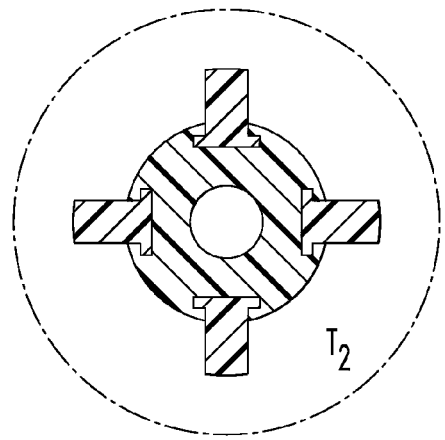

FIGS. 18a-18c show how the materials 123,124 may be combined via a mechanical interlocking means. A sleeve 128 having shape memory polymer material 124 is shown including components 129 having a different shape memory polymer material, such as 123, and a through hole 128a. When a heating device is placed in the through hole 128a and heated to temperature T1, component 129 expands to fixate the sleeve 128 to the bone 125. Likewise, when the temperature of the heating device reaches T2, the sleeve 128 shrinks resulting in the sleeve 128 and the components 129 being pulled from the sides of the cavity, thereby allowing removal of the sleeve 128 from the bone 125.

For the purposes of this disclosure, the internal fixation devices described above may be manufactured from a metal, such as titanium, titanium alloys, steel, stainless steel, cobalt-chromium alloys, tantalum, magnesium, niobium, nickel, nitinol, platinum, silver, and combinations thereof. Other metals known to one of ordinary skill in the art could also be used. The device may also be manufactured from a resorbable or non-resorbable polymer material and may be the same polymer material used on the shaped interface portion, as described above, or another type of polymer material.

Example 1

Material 1: Polylactide (PLLA-co-DL (70/30) copolymer containing 35% (wt/wt %) calcium carbonate filler pellets were placed into a metal mould, heated at 150° C. and compacted at 160° C. to produce a billet having a diameter of 20 mm and a length of 100 mm. The billet was heated to 65° C. and pulled through a 20 mm die at a rate of 20 mm per minute to produce an orientated rod having a final diameter of 11 mm (draw ratio of 3·25).

Material 2: PETG pellets (polyethylene terephthalate glycol) were placed into a metal mould, heated to 250° C., compacted, and cooled to room temperature to generate a 30 mm diameter billet. The billet was heated to 95° C. and then pulled through a 15 mm die to generate an orientated rod having a final diameter of 13·8 mm (draw ratio of 4.7).

Figure 19A:
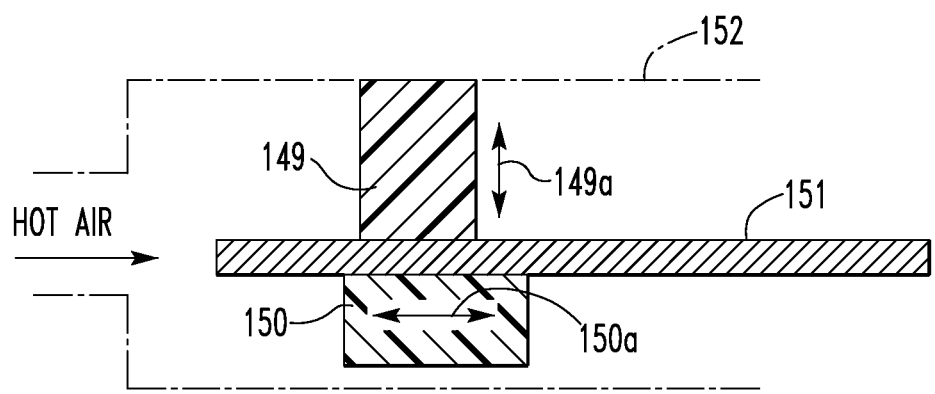
FIGS. 19-21 show a seventh method of fixating and removing an internal fixation device to and from a bone.
Figure 19B:
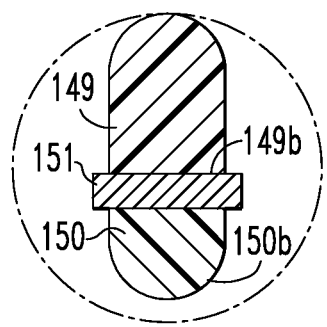

As shown in FIGS. 19a and 19b, samples of the drawn materials (material 1 represented by 149 and material 2 represented by 150) were then placed in a glass tube 152 in such a way that their draw directions were perpendicular to each other, as represented by arrows 149a and 150a. The inner diameter of the tube 152 is 40 mm. A rod 151 was subsequently placed between the samples 149,150. An end 149b of material 149 was machined to be flat and an end 150b of material 150 was machined to be rounded, as shown in FIG. 19b.

Figure 20:
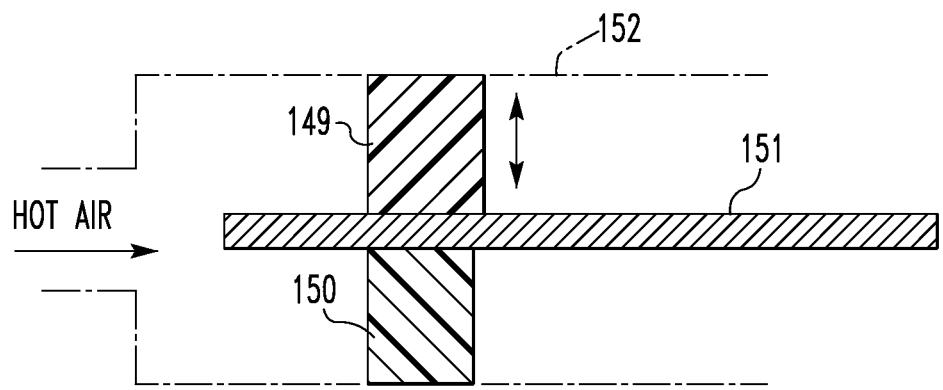
Figure 21:
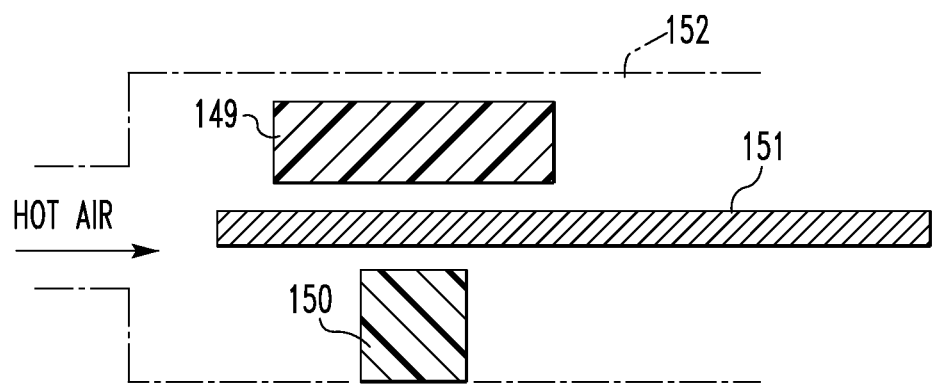

Hot air at a temperature of T1 (80° C.) was then blown into the glass tube 152 for 5 minutes. This caused material 150 to relax, as shown in FIG. 20, reducing its length in the orientation direction but increasing its diameter. However material 149 did not change its dimensions, due to the much higher relaxation temperature, resulting in the rod 151 becoming locked in place. It was found that if a flat surface was used on material 149 and a rounded end on material 150, the rod was held with considerable force and could support a weight of 2 kg. Hot air at a temperature of T2 (110° C.) was then blown into the glass tube 152. This caused material 149 to relax, as shown in FIG. 21, reducing its length in the orientation direction and thus releasing the rod 151 for removal.

Example 2

Two shape memory polymer sleeves were prepared with each sleeve having an external diameter of 15 mm, a length of 27 mm, and an internal diameter of 4.7 mm. A stainless steel sleeve having an external diameter of 4.7 mm and an internal diameter of 4 mm was placed within the sleeve to accommodate a heater probe. One sleeve was wrapped in 0.65 mm diameter polycaprolactone (PCL) fibre over the middle ⅔ of its length.

The sleeves were each placed in a 17.3 mm diameter, 4 cm deep hole in a block of 20 pcf sawbone. The sleeves were then relaxed by placing a 4 mm diameter heating probe in the stainless steel sleeve. The probe was heated to 175° C. for 15 minutes. The probe was then removed and the samples allowed to cool to room temperature. Mechanical testing of the samples was done by a push-out test. The sawbone block was mounted on a ring support and the sleeve pushed out using an 8 mm Allen key, at a speed of 1 mm/min. The peak force required to move the sleeve is shown in Table 1.

TABLE 1

| Sample | Peak pushout force |
| --- | --- |
| SMP plug (no PCL coating) | 208 N |
| SMP plug containing PCL fibre coating | 1586 N |

A sleeve was produced using the above method and subsequently placed in sawbone. The sawbone was heated to 80° C. for 10 min in a heated chamber. The fixation force was measured by applying a force to the heated sleeve. Mechanical testing of the samples was done using a push-out test. The sawbone block was mounted on a ring support and the plug pushed out, using an 8 mm Allen key, at a speed of 1 mm/min. The peak force required to move the sleeve was 20 N.

Figure 22A:
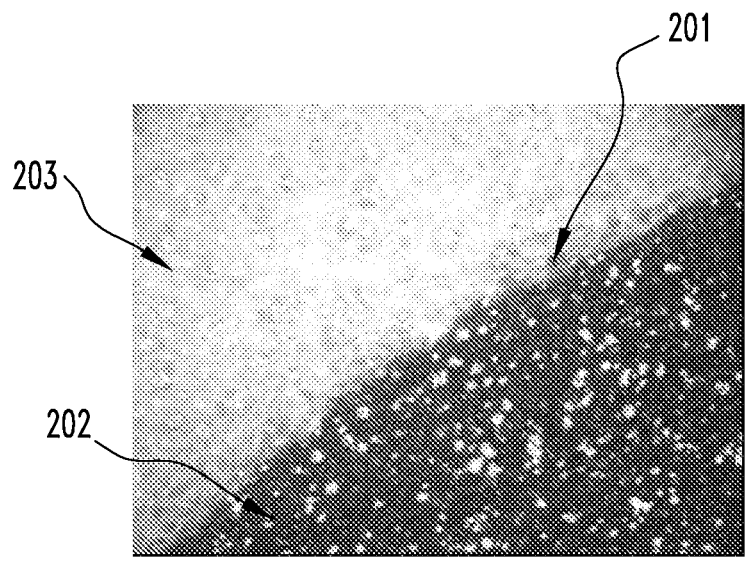
FIG. 22a shows the interface between shape memory polymer material and saw bone.
Figure 22B:
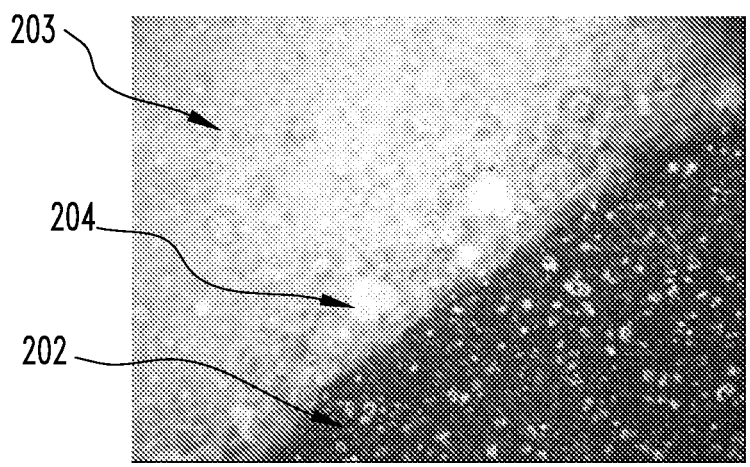
FIG. 22b shows polycaprolactone located within the bone and between the bone and shape memory polymer material.

FIG. 22a shows the interface 201 between the shape memory polymer sleeve 202, having the polycaprolactone (PCL) fiber (not shown), and the saw bone 203. FIG. 22b shows the shape memory polymer sleeve 202 and the saw bone 203 after activation of the sleeve 202. As shown in FIG. 22b, the PCL 204 has melted and has been integrated into the saw bone 203. As evidenced by the above data, the addition of the PCL to the shape memory polymer sleeve improves fixation of the sleeve to the bone by melting, upon application of energy to the sleeve, and integrating with the bone, thereby acting as an interfacial adhesive agent. Upon reheating, the polycaprolactone melts agains to provide a low viscosity lubricious layer that allows for removal of the shape memory polymer sleeve.

In view of the foregoing, it will be seen that the several advantages of the disclosure are achieved and attained.

The embodiments were chosen and described in order to best explain the principles of the present disclosure and its practical application to thereby enable others skilled in the art to best utilize the disclosure in various embodiments and with various modifications as are suited to the particular use contemplated.

As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of deforming a shape memory polymer material comprising:
   providing a heating device including multiple heating probes;
   providing a single sleeve component formed of a shape memory polymer material, the single sleeve component including multiple holes;
   inserting the multiple heating probes into the multiple holes located in the single sleeve component; and
   delivering heat to the multiple heating probes, wherein the heat from the multiple heating probes causes the shape memory polymer material of the single sleeve component to expand.

2. The method of claim 1, wherein the multiple holes comprise through holes extending entirely through the single sleeve component and along an entire length of the single sleeve component.

3. The method of claim 1, the central portion of the single sleeve component is solid and does not include any of the multiple holes.

4. The method of claim 1, further comprising outwardly expanding the single sleeve component evenly along an entire length of the single sleeve component upon heating of the shape memory polymer material by the multiple heating probes.

5. The method of claim 1, wherein the shape memory polymer material comprising a bioactive agent.

6. The method of claim 5, wherein the bioactive agent comprising at least one selected from the group consisting of a bone morphogenic protein, an antibiotics, an anti-inflammatory agent, an angiogenic factor, an osteogenic factor, monobutyrin, an omental extract, thrombin, a modified protein, a platelet rich plasma/solution, a platelet poor plasma/solution, a bone marrow aspirate, a living cell, a preserved cell, a dormant cell, and a dead cell.

7. The method of claim 1, wherein the shape memory polymer material comprising a reinforcing material.

8. The method of claim 7, wherein the reinforcing material comprising at least one selected from the group consisting of a glass fiber, a carbon fiber, a polymeric fiber, a ceramic fiber, and a ceramic particulate.

9. The method of claim 1, wherein the single sleeve component includes a peripheral portion surrounding a central portion, the multiple holes located in the peripheral portion of the single sleeve component.

10. A method of deforming a shape memory polymer material comprising:
    providing a heating device including multiple heating probes in-situ disposed within multiple holes located in a single sleeve component, the single sleeve component formed of a shape memory polymer material; and
    delivering heat to the multiple heating probes disposed within the multiple holes located in the single sleeve component, wherein the heat from the multiple heating probes causes the shape memory polymer material of the component to expand.

11. The method of claim 10, wherein the shape memory polymer material comprising a bioactive agent.

12. The method of claim 11, wherein the bioactive agent comprising at least one selected from the group consisting of a bone morphogenic protein, an antibiotics, an anti-inflammatory agent, an angiogenic factor, an osteogenic factor, monobutyrin, an omental extract, thrombin, a modified protein, a platelet rich plasma/solution, a platelet poor plasma/solution, a bone marrow aspirate, a living cell, a preserved cell, a dormant cell, and a dead cell.

13. The method of claim 10, wherein the shape memory polymer material comprising a reinforcing material.

14. The method of claim 13, wherein the reinforcing material comprising at least one selected from the group consisting of a glass fiber, a carbon fiber, a polymeric fiber, a ceramic fiber, and a ceramic particulate.

15. The method of claim 10, wherein the single sleeve component includes a peripheral portion surrounding a central portion, the multiple holes located in the peripheral portion of the single sleeve component.

16. A method of deforming a shape memory polymer material comprising:
    providing a heating device including multiple heating probes in-situ disposed within multiple holes located in a peripheral portion of the component surrounding a central portion of the component, the component formed of a shape memory polymer material;
    delivering heat to the multiple heating probes disposed within the multiple holes located in the peripheral portion of the component, wherein the heat from the multiple heating probes causes the shape memory polymer material of the component to expand; and
    wherein the central portion of the component is solid and does not include any of the multiple holes.

17. A method of deforming a shape memory polymer material comprising:
    providing a heating device including multiple heating probes in-situ disposed within multiple holes located in a peripheral portion of the component surrounding a central portion of the component, the component formed of a shape memory polymer material;
    delivering heat to the multiple heating probes disposed within the multiple holes located in the peripheral portion of the component, wherein the heat from the multiple heating probes causes the shape mer material of the component to expand; and
    outwardly expanding the component evenly along an entire length of the component upon heating of the shape memory polymer material by the multiple heating probes.

18. The method of claim 17, wherein the multiple holes located in the peripheral portion of the component comprise through holes extending entirely through the component along the entire length of the component.

19. A method of deforming a shape memory polymer material comprising:
    providing a heating device including multiple heating probes;
    providing a shape memory polymer material including multiple holes;
    inserting the multiple heating probes into the multiple holes;
    delivering heat to the multiple heating probes, wherein the heat from the multiple heating probes causes the shape memory polymer material to expand;
    providing a single sleeve component formed of the shape memory polymer material, the sleeve component defining the multiple holes that receive the multiple heating probes of the heating device;
    wherein the heat from the multiple heating probes causes the sleeve component to change shape.

20. A method of deforming a shape memory polymer material comprising:

providing a heating device including multiple heating probes in-situ disposed with a shape memory polymer material;

delivering heat to the multiple heating probes, wherein the heat from the multiple heating probes causes the shape memory polymer material to expand; and providing a single sleeve component formed of the shape memory polymer material, the sleeve component defining multiple holes that receive the multiple heating probes of the heating device; and wherein the heat from the multiple heating probes causes the sleeve component to change shape.

* * * * *